US012611369B2

(12) United States Patent
Shoseyov et al.

(10) Patent No.: US 12,611,369 B2
(45) Date of Patent: Apr. 28, 2026

(54) SKIN MIMICRY COMPOSITIONS AND IMPLANTS

(71) Applicant: Yissum Research Development Company of the Hebrew University of Jerusalem Ltd., Jerusalem (IL)

(72) Inventors: Oded Shoseyov, Shoham (IL); Chen Nowogrodski, Shoham (IL); Yaniv Damatov, Rehovot (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 232 days.

(21) Appl. No.: 18/712,146

(22) PCT Filed: Nov. 23, 2022

(86) PCT No.: PCT/IL2022/051248
§ 371 (c)(1),
(2) Date: May 21, 2024

(87) PCT Pub. No.: WO2023/095134
PCT Pub. Date: Jun. 1, 2023

(65) Prior Publication Data

US 2025/0025401 A1 Jan. 23, 2025

Related U.S. Application Data

(60) Provisional application No. 63/264,536, filed on Nov. 24, 2021, provisional application No. 63/264,534, filed on Nov. 24, 2021.

(51) Int. Cl.
*A61K 8/65* (2006.01)
*A61Q 1/02* (2006.01)
*A61Q 19/00* (2006.01)
*C07K 14/47* (2006.01)

(52) U.S. Cl.
CPC .................. *A61K 8/65* (2013.01); *A61Q 1/02* (2013.01); *A61Q 19/00* (2013.01); *C07K 14/4741* (2013.01); *A61K 2800/43* (2013.01)

(58) Field of Classification Search
CPC .................................. A61Q 1/02; A61Q 19/00
USPC ........................................................... 424/63
See application file for complete search history.

(56) References Cited

PUBLICATIONS

Posati et al., "Mild and Effective Polymerization of Dopamine on Keratin Films for Innovative Photoactivable and Biocompatible Coated Materials." Macromolecular Materials and Engineering 2018; 303, 1700653. DOI:10.1002/mame.201700653 (Year: 2018).*

(Continued)

*Primary Examiner* — Walter E Webb
(74) *Attorney, Agent, or Firm* — Vorys, Sater, Seymour and Pease, LLP; Maryellen Feehery Hank

(57) ABSTRACT

Provided are systems, compositions, methods and devices for manufacturing artificial skin substitutes and related products mimicking the morphology and appearance of human skin. Applications of the invention pertain to the fields of regenerative medicine and pharma with products that can support tissue replacement and tissue engineering. The most immediate applications pertain to the field of cosmetics with the development of pigmented compositions that can be incorporated in various skin care and cosmetic foundation products.

20 Claims, 10 Drawing Sheets

(56) References Cited

PUBLICATIONS

Cavallini et al., "Melanin and Melanin-Like Hybrid Materials in Regenerative Medicine", Nanomaterials, 2020, vol. 10, No. 8, Aug. 3, 2020, p. 1518 (33 pages).
Jaber et al., "A New Nanocomposite: L-DOPA/Laponite", Journal of Physical Chemistry Letters, 2009, vol. 1, No. 1, Nov. 6, 2009, pp. 85-88.
Solano, "Melanin and Melanin-Related Polymers as Materials with Biomedical and Biotechnological Application—Cuttlefish Ink and Mussel Foot Proteins as Inspired Biomolecules", International Journal of Molecular Sciences, 2017, vol. 18, No. 7, Jul. 18, 2017, (18 pages).
Zhao et al., "Anisotropic hair keratin-dopamine composite scaffolds exhibit strain-stiffening properties", Journal of Biomedical Materials Research Part A, 2021, vol. 110, No. 1, Jul. 13, 2021, pp. 92-104.

* cited by examiner

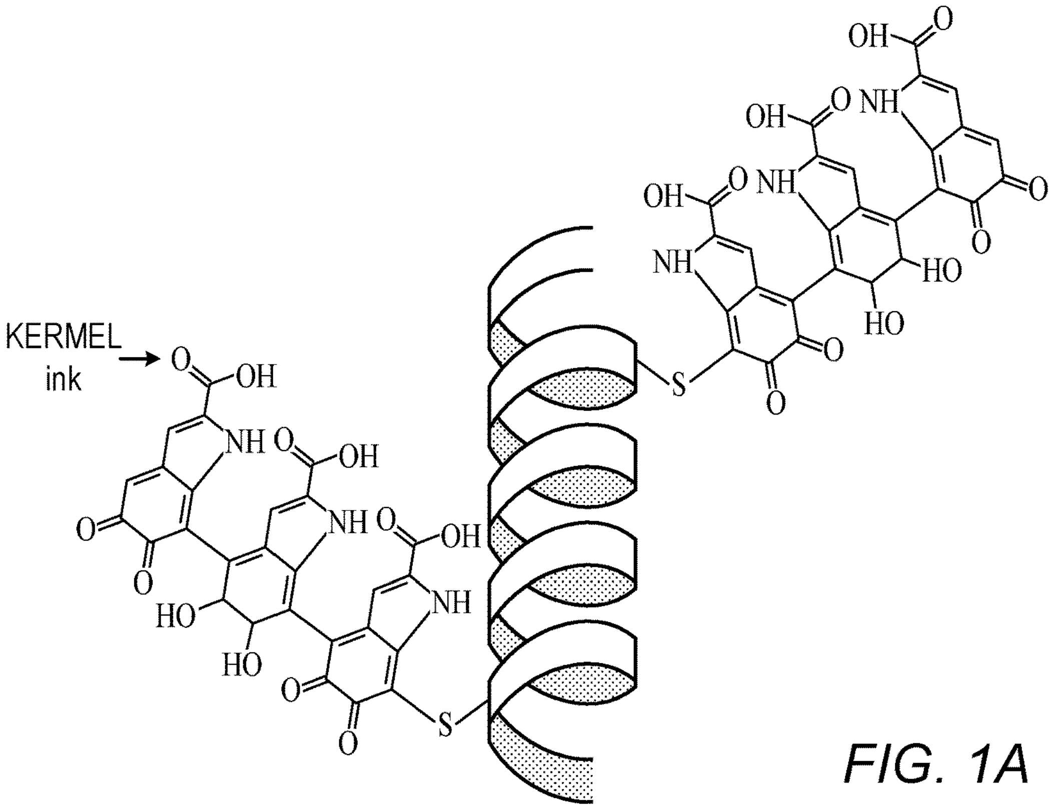
*FIG. 1A*
*FIG. 1B*
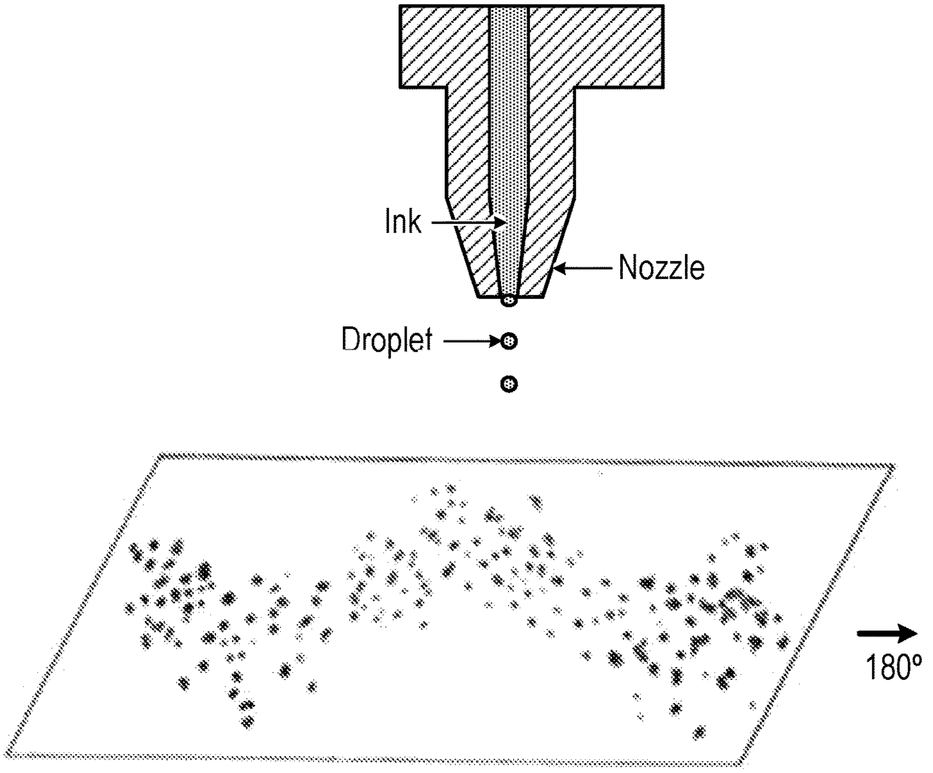

FIG. 10A
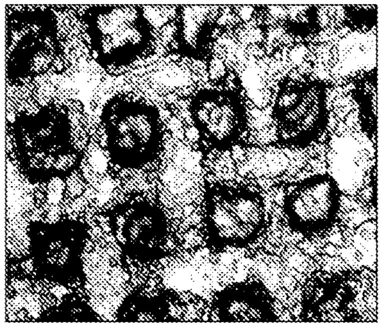
FIG. 10B
FIG. 10C
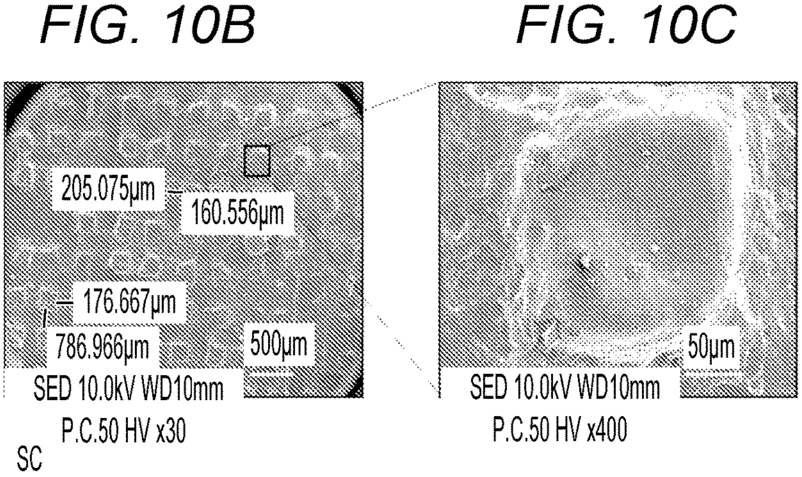
FIG. 11
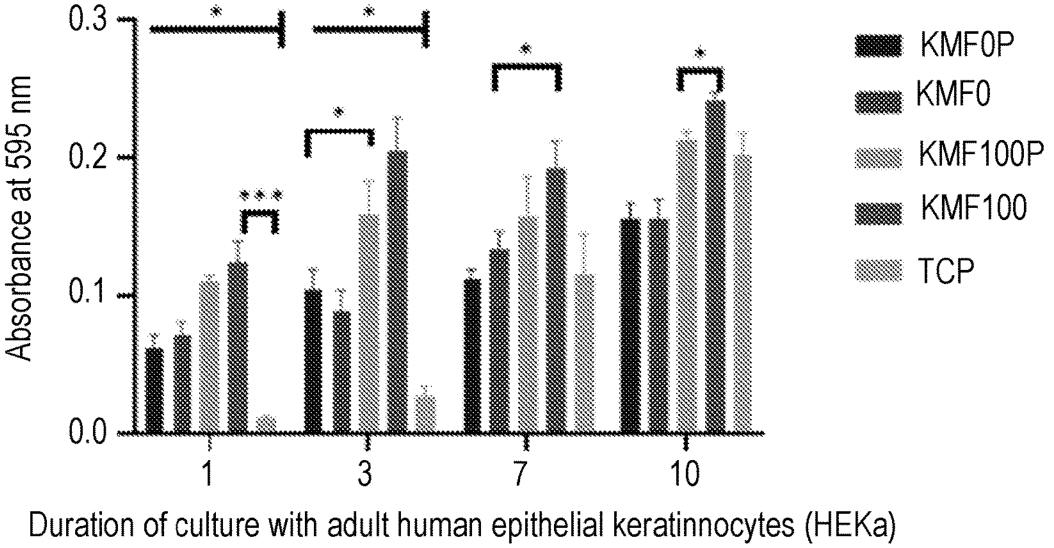

SKIN MIMICRY COMPOSITIONS AND IMPLANTS

TECHNOLOGICAL FIELD

The invention generally belongs to the field of tissue engineering and specifically to the field of artificial skin substitutes and products mimicking the morphology and/or appearance of human skin. The invention describes compositions and constructs that can form the basis for various types of skin substitutes, the methods of making and applications thereof in cosmetics and pharma, and tissue replacements and engineering.

BACKGROUND

The skin is an organ with multiple physiological functions which is extremely responsive to fluctuating environment and is the first and the foremost to be impacted by the signs of aging, external insults and various types of diseases. Medical and cosmetic industries, each for its own purposes, have pushed towards the development of various skin substitutes, a "second skin" or electronic skin (e-skin), typically made of topically applied wearable skin-conforming materials mimicking the human skin in terms of complexion, elasticity, tribology and tactile sensing. Despite apparent advances in this direction, many of the new technologies are still incomplete in their abilities to provide a desirable, cost-effective and useful product.

Polydimethylsiloxane (PDMS), for example, one of the convenient choices for a substitute skin material due to its elasticity, durability and non-toxicity, has a critical downside for being costly and non-biodegradable. More biodegradable and biocompatible alternatives include collagen, elastin and keratin, and specifically the hydrolyzed keratin—a solubilized keratin produced by oxidation/reduction processes that can be easily fabricated into hydrogels, films, fibers, composites and inks. Nonetheless, the existing experience with these materials, even with the assisting 3D-printing technologies, all fall short of providing a genuine-looking, dependable, reproducible and commercializable skin product.

A specific problem is incorporation of colour and the ability to produce a skin substitute that is totally matching in colour and tone to the skin of a given individual. Current skin color technologies largely use melanin as a structural color component, more precisely, various combinations of eumelanin (brown/black) and pheomelanin (yellow/red), the two main melanin subtypes, to provide the full-scale skin color palette.

Color is one of the main reasons for wearing cosmetics. Pigmented compositions are widely used in cosmetic products to even skin texture and tone and to conceal minor skin imperfections. They can be in the form of liquid or cream suspensions, emulsions, gels, pressed powders or anhydrous oils or waxes, typically made of various synthetic pigments, humectants, emulsifiers.

One problem with color cosmetics is that they must be very carefully formulated to provide maximum effect and maximum safety. Current trends in color cosmetics have tried to address safety with products made natural biocompatible and biodegradable plant materials, and materials obtained from other sources. In terms of effect, water-based foundations generally provide better coverage and good skin-feel, although they are less compatible with oily skin complexions and incorporation of poorly water-soluble actives.

Another problem, as has been noted, is color matching and the ability to accurately match the color and tone of a product to the skin complexion of any given individual. A common solution, so far, has been to leave the matching decision to end-users in offering a series of products with pre-set skin tones and undertones. Another opinion holds that to provide a perfectly matching foundation or cosmetic product, the color matching must be a fully customized and digitized process. Some precedents have been made in this direction using imaging and input data on an individual's skin completion, demographics and lifestyle. This approach, however, implies the ability to produce a versatility of colors across the entire range of skin color palette.

More generally, color is only one outer aspect of skin mimicking. Another aspect to be considered is the structural and functional arrangement of multiple cell types and non-cellular extracellular matrix components (ECM) making the skin such a highly complex organ. The human skin is roughly divided into two main layers: (1) the epidermis—an outer protective layer predominantly composed of keratinocytes and melanocytes and their keratin and melanin products, and lipids; and (2) the dermis—an inner layer composed of fibroblast, proteins, glycosaminoglycans, collagen, fibrin, hyaluronic acid, blood vessels, hair follicles, sweat glands, and other types of cells. The outermost epidermal layer is the stratum corneum (SC)—a densely packed layer of keratinocytes, which owing to its distinctive thickness (50-1500 μm) and elastic modulus (about 1.5 MPa) serves as a barrier against water loss and various infections.

The two main components responsible for the outer skin appearance are keratin and melanin. Keratin is a keratinocytes-derived structural protein that can be in soft or hard forms that differ by their cysteine content and the ability to form disulfide bonds. The hard keratins of mammals are exclusively alpha helix structures making the fibrous components of the skin, hair and wool. Melanin is a pigment initially produced by melanosomes in melanocytes, which upon maturation migrate to keratinocytes where they make visible pigmentation. It is the main color determining component of the skin and hair in mammals and other animals. It also serves as a protective shield against UV radiation and bacterial infections.

The basal layer of the epidermis, also Rete Ridge (RR), has a characteristic papillary structure that is essential for its increased surface exposure and anchoring of the dermo-epidermal junction. During normal epidermal growth, keratinocytes at the lower epidermis are pushed toward the upper SC layer where they undergo keratinization and cornification processes, leading to loss of cell viability and other modifications providing the skin its characteristic appearance. In other words, any damage to RR and disruption of the basal epidermis morphology, such as in deep skin injury for example, is ultimately reflected in structural abnormalities of the SC and the epidermis in general.

A second skin should be, ideally, a substantially close facsimile of the composition and spatial organization of the natural skin. Certain skin substitutes reproducing partial RR and SC properties have been developed using various types of skin models and tissue engineering technologies [1-8]. Specific progress has been made in the field of polymeric peptide pigments mimicking skin colors and tones [9-12].

The technology disclosed in this application offers a comprehensive multilayered solution to all aspects of skin mimicry in the form of a series of highly refined products that can be fully customized and adapted to the traits, conditions and color of the skin of a given individual, and further, fully controllable and digitizable methods for producing such products and examples of potential applicability thereof.

REFERENCES

1. Posati T et al. Developing keratin sponges with tunable morphologies and controlled antioxidant properties induced by doping with polydopamine (PDA) nanoparticles Materials and Design 2016, 110:475-484.
2. Liu Y et al. Lab-on-Skin: A review of flexible and stretchable electronics for wearable health monitoring ACS Nano 2017, 11(10):9614-9635.
3. De Guzman K and Morrin A. Screen-printed tattoo sensor towards the non-invasive assessment of the skin barrier proof-of-concept: 3D bioprinting of pigmented human skin constructs. Electroanalysis 2017, 29(1):188-196.
4. Posati T et al. Mild and effective polymerization of dopamine on keratin films for innovative photoactivable and biocompatible coated materials. Macromol Mat Eng 2018, 303(8):1700653.
5. Ng W L et al. Proof-of-concept: 3D bioprinting of pigmented human skin constructs. Biofabrication 2018, 10(2):025005.
6. Pandala N et al. Screen printing to create 3D tissue models. ACS Appl Bio Mater 2020, 3(11):8113-8120.
7. Zeng W et al. Wool keratin photolithography as an eco-friendly route to fabricate protein microarchitectures. ACS Appl Bio Mater 2020, 3(5):2891-2896.
8. Zhao Z, Chua H M, Goh B H R, Lai H Y, Tan S J, Moay Z K, Setyawati M I, Ng K W. Anisotropic hair keratin-dopamine composite scaffolds exhibit strain-stiffening properties. J Biomed Mater Res A. 2022 January; 110(1): 92-104.
9. Lampel A et al. Polymeric peptide pigments with sequence-encoded properties. Science 2017, 356(6342): 1064-1068.
10. Arl M et al. Tattoo inks: Characterization and in vivo and in vitro toxicological evaluation. J Hazard Mater 2019, 364:548-561.
11. Han X et al 2020. Keratin-dopamine conjugate nanoparticles as pH/GSH dual responsive drug carriers. J Biomater Sci Polym Ed 2020, 31(18)
12. Lampel A et al. Melanin-inspired chromophoric microparticles composed of polymeric peptide pigments. Angewandte Chemie International Ed 2021, 60(14)

GENERAL DESCRIPTION

Humans have been engaged in skin mimicking since the dawn of history, starting from masks and makeups and up to skin replacement by modern medicine. Skin mimicking, however, has proved to be very difficult due to the abundance of structural and functional elements making the skin and their complex spatial arrangement. The two structures that are crucial for skin functionality and appearance are SC and RR, the first by defining the outward skin properties of the and the second by determining the inner arrangement of skin layers. The conventional skin models, using polymeric matrixes either with or without cells, generally disregard these structures and therefore provide only uniform single tone substitutes deprived of natural and individual skin attributes.

The present technology offers a novel disruptive approach to skin mimicry that combines an artificial bio-based epidermis model epitomizing the native skin morphology and a unique structural skin pigment that can be produced in a plethora of colors and tones mimicking the entire range of human skin complexions. The skin pigment component can be used alone to provide a highly adaptable skin coloring material that can be perfectly matched to the specific complexion of an individual skin, and in combination with 2D and 3D printing technologies, can be incorporated into a series of secondary products, e.g., films, hydrogels and high viscosity inks, to be used in the fabrication of skin constructs with partial or complete mimicking of more complex skin characteristics.

In other words, the strength of the present invention is in providing a simple fully customized and holistic solution to skin mimicry, starting from skin coloring compositions that can be incorporated into many cosmetic and beauty products and up to more sophisticated skin mimicking structures serving as highly refined functional skin substitutes. And all these, with essentially “green chemistry” using water and enzymes and natural biocompatible materials and almost no organic solvents. It is therefore expected, as was demonstrated in this application, that the products of the invention will not interfere with surrounding skin structures and the natural skin growth in situ, and thus can provide effective methods masking replacing, reconstructing, protecting and/or treating skin imperfections and skin damage.

In summary, the advantages of this technology are in:

(1) ability to provide a unique naturally based pigment, or a pigmented composition comprising thereof, that can serve as a basis for producing an extended calculated color palette to cover the entire range of natural skin colors and tones, referred to herein as a keratin/melanin compound or conjugate (KERMEL); and (2) to provide an authentic custom-made substitute skin product having a general skin-like morphology in terms of SC and RR, and further, the specific pigmentation, texture and outward appearance of a given individual skin, referred to as—a portable epidermis model (PEM);

this, while KERMEL may be used alone or in combination with PEM to provide a comprehensive highly personalized and authentic skin mimicking system.

The application further provides a proof-of-concept for (1) and (2). Specifically, using L-dopa as a starting material of eumelanin and pheomelanin and hydrolyzed keratin, the inventors have demonstrated the ability to produce KERMEL—a new pigment molecule, which is essentially a keratin/melanin chromophore nanoparticle produced by polymerization of L-Dopa on cysteine residues of keratin backbone by enzymatic oxidation, for example. The inventors have further shown that KERMEL preserves the core properties of keratin and the two melanin color configurations and can be modulated to provide a wide range of natural skin tones. (Example 1)

More specifically, KERMEL is a novel material constructed of a keratin backbone and melanin in two color configurations, eumelanin (black/brown) and pheomelanin (yellow/red), the combination of which determines the color and other properties of the resulting product. The color of KERMEL can be controlled throughout the synthesis process by the content of the two melanin residues, and eventually, can be translated into a fully digitized skin color library. The feasibility of such digitized ready-to-use skin color library was further demonstrated using mixes of KERMEL and synthetic eumelanin/pheomelanin to produce a calculated color palette that could potentially cover the entire range of natural skin tones.

It has been further demonstrated that using a novel high viscous keratin ink (HVKI) and additive manufacturing KERMEL can be fabricated into highly durable and adaptable films (KMFs). KMFs are essentially a facsimile of SC, and together with the ability to control color, they provide a simple tool for outer skin replacement or a specifically tailored artificial skin graft mimicking the essential characteristics of a given individual skin. (Example 2)

It has been further demonstrated that using the same methodological approach, KERMEL, HVKI and additive manufacturing, it was possible to produce a more advanced composite material reproducing the entire epidermal 3D structure, morphology and pigmentation, i.e., a portable epidermis model (PEM). In a pilot trial, it was shown that the resulting PEM was consistent with the expected structural and functional properties of the complex epidermis in terms of SC and RR structures and the ability to support a 3D-pattern controlled cell growth along 2D layout, other words, was consistent with a viable epidermis-like structure. (Example 3)

In summary, the presently proposed inventive concept offers an inclusive multilayered approach to skin mimicking and engineering with the design and development of a new skin mimicking system that can be used in part or as a whole for a variety of medical and aesthetic applications, such as skin masking, wound dressing, skin grafting, and more broadly, tissue engineering and replacement, cornea replacement, and other applications. In skin masking, a partial skin mimicking system (KERMEL) provide a "green" fully controllable digitizable composition that can be incorporated in a wide range of skin care and beauty products so as to find a perfect match to a given individual skin and hair color and tone. In skin grafting, a complete skin mimicking system (KERMEL and PEM) can mimic or serve as a template for producing a facsimile of a complete functional dermal-epidermal junction so as to provide an authentic and viable skin substitute.

BRIEF DESCRIPTION OF THE DRAWINGS

FIG. 10 illustrates another application of KERMEL using HVKI for producing high resolution Rete Ridge structures on glass. Figure shows various resolutions of 1:1 keratin: glycerol HVKI screen prints on glass, including (a) a photo image of the screen print; (b) a light microscopy image of the same; and (c) an SEM image and magnification of the same, with a distinct 3D shape.

FIG. 11 illustrates the ability to produce a viable reconstructed human epidermis (RhE) using the presently developed methods and tools. Figure shows the duration and proliferation of human epithelial keratinocytes (HEK) on KMFs as revealed by MTT assay relative to TCP control.

DETAILED DESCRIPTION OF EMBODIMENTS

The present technology delivers on two important aspects of skin mimicking: biocompatibility and personalization. To that end, it provides three important products:

i. A ready-to-use fully digitizable keratin/melanin color library using novel keratin-melanin (KERMEL) chromophore nanoparticles and synthetic eumelanin/pheomelanin;
ii. High Viscous Keratin Ink (HVKI) incorporating KERMEL, which with the aid of additive manufacturing technologies permits fabrication of product with varying degree of structural complexity, e.g., films, hydrogels and high viscosity inks.
iii. Portable Epidermis Model (PEM) reproducing the structural complexity of the stratum corneum (SC) and the papillary dermo-epidermal junction with KERMEL incorporated/deposited onto the outer SC layer.

The advantages of the technology should be appreciated on a number of levels:

- it uses biomaterials naturally found in human skin and hair;
- it is fully controllable in terms of the desired color and tone of the end-product;
- it provides pigmented products across the entire range of the natural human skin colors and tones, which could be translated to a calculated color;
- it is fully digitizable; and
- it is fully adaptable to provide an end-product that is fully matching to the texture, color and tone of a given individual skin or hair.

Melanin is the main pigment protein that dictates the color and tone of skin and hair in mammals. Keratin, on the other hand, is the main structural protein of skin and hair, and it further supports the presence of melanin. Eumelanin (brown-black pigment) and Pheomelanin (yellow-red pigment), the two main melanin subtypes, are synthesized from the same building block by enzymatic oxidation. The latter has an addition of cysteine impacting its final structure.

Figure 1C:
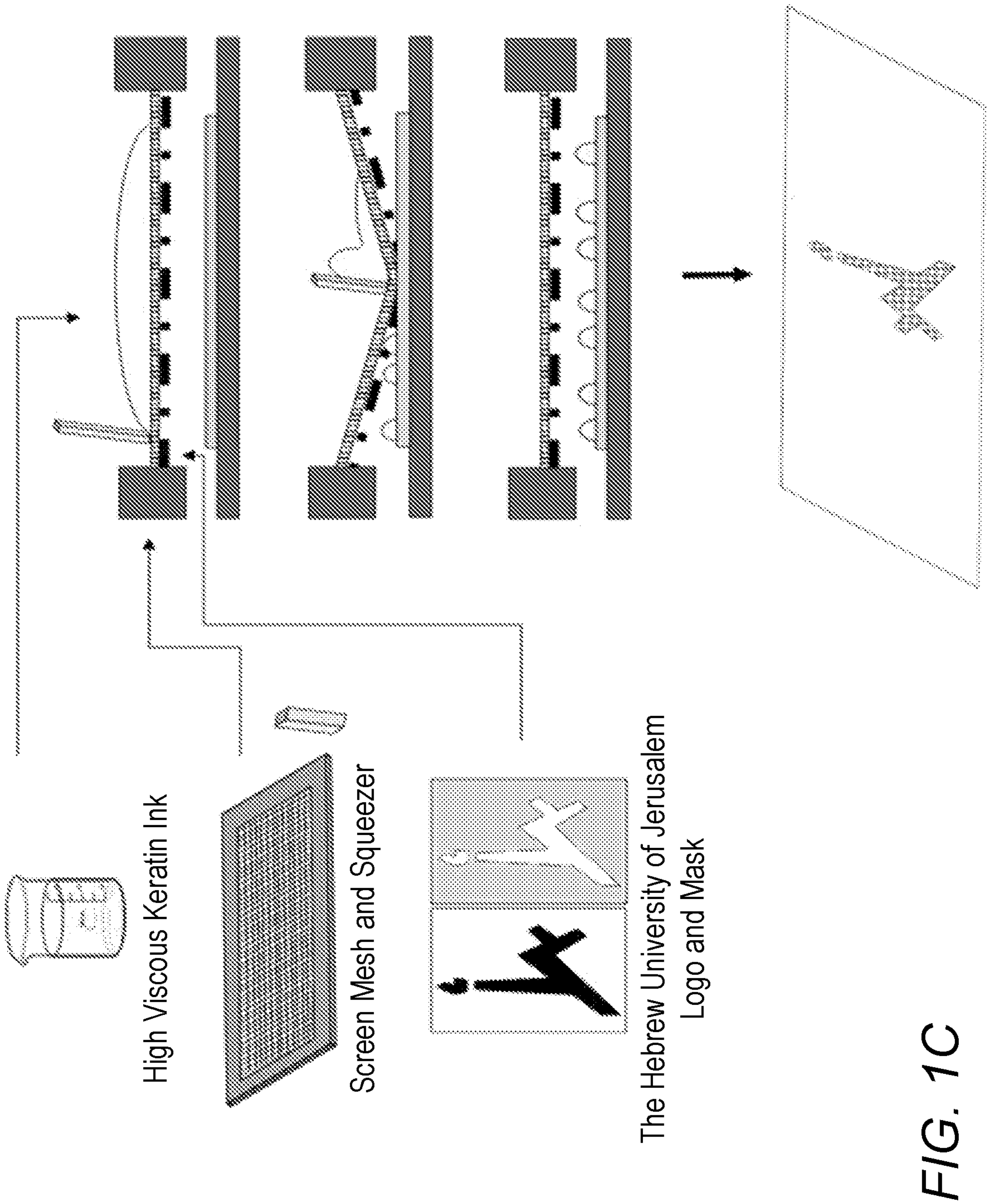
FIG. 1 illustrates (a) the process of preparing of the KERMEL pigment or ink from the starting keratin/melanin materials; (b) the process of preparing and jet printing the KERMEL ink onto the KMF films; and (c) the process of preparing composite patterns and structures by screen printing the HVKI bio-ink onto KMF.

Building on the presence of cysteine in hydrolyzed keratin and using L-Dopa and enzymatic oxidation with design of experiment (DOE) definitive screening design model, the inventors have succeeded to synthetize new KERMEL compounds/conjugates that form chromophores nanoparticles. A putative mechanism underlying the keratin/L-Dopa polymerization is illustrated in FIG. 1. Essentially, the mechanism uses oxidation of L-Dopa via reaction with the thiol group on the hydrolyzed keratin backbone, which is analogous to the reaction with cysteine. The polymerization of L-Dopa on the keratin backbone grants the resulting molecule its color. Importantly, the new KERMEL molecule preserves hydrolyzed keratin properties with the two melanin color configurations, and therefore allows to produce a wide range of colors and tones across human skin and hair color palette. As has been demonstrated in this application, the range of colors can be further expanded and refined by the addition of synthetic eumelanin/pheomelanin, and eventually translated to a digitized color palette.

Thus, at the core of the present technology is a novel compound (KERMEL) that consists essentially or comprises a keratin backbone bonded to or "decorated with" a plurality of melanin moieties. Each of the melanin moieties has a structure derived from oxidation of Dopa onto a hydrolyzed cysteine moiety part of the keratin backbone.

The term "keratin" encompasses herein Type I keratins, i.e., the acidic, low molecular weight keratins encoded in human on chr. 17, and Type II keratins, i.e., the basic or neutral high molecular weight keratins encoded inn humans on chr. 12 q. Both types are present in all mammalian epithelial cells and form pairs of heterotypic Type I/Type II keratin chains constructing the intra-cytoplasmatic cytoskeleton. This term predominantly refers herein to the alpha-keratin constructing the epidermis, the hair, horns and nails of mammals.

In numerous embodiments the keratin is an alpha-keratin or a part thereof.

In some embodiments the keratin can be a recombinant protein, meaning a keratin produced in the lab by recombinant genetic technologies.

In some embodiments the keratin can be a beta-keratin or a part thereof.

The terms "melanin" or "melanin unit" or "melanin moiety" encompass herein any structural unit or a part of a molecule derived from a melanin pigment molecule, either a natural or a synthetic derivative thereof. This term encompasses herein moieties or units derived from eumelanin, pheomelanin, neuromelanin, allomelanin and pyomelaninis, the main melanin types.

In numerous embodiments each of the melanin moieties has a structure derived from oxidation of Dopa onto a hydrolyzed cysteine moiety part of the keratin backbone.

In numerous embodiments the keratin backbone can constructed of a modified hydrolyzed keratin that is covalently associated with a plurality of melanin units.

The term "hydrolyzed keratin" encompasses herein any hydrolysate of keratin protein derived from acid, enzyme, and other method of hydrolysis.

In some embodiments the keratin backbone comprises a plurality of sulfur groups, with a portion thereof being covalently associated with a plurality of melanin units. Sulfur groups, predominantly due to the sulfur-containing amino acid cysteine, permit the formation of disulfide bridges, which together with the intra- and intermolecular hydrogen bonds confer additional strength and rigidity by permanent, thermally stable crosslinking.

A KERMEL compound can be further articulated in terms of a keratin backbone that is a keratin-melanin conjugate derived from L-Dopa polymerization on a keratin backbone that comprises a plurality of melanin units covalently associated with a keratin molecule.

In numerous embodiments the melanin unit can comprise a melanin selected from at least one of eumelanin, pheomelanin, neuromelanin, allomelanin and pyomelaninis or a derivative of thereof, or any combination thereof.

In some embodiments the melanin can be eumelanin or pheomelanin or a derivative or a combination thereof.

In some embodiments the melanin unit can comprise one or more repeating units selected from L-tyrosine, L-dopa, L-dopaquinone, L-leucodopachrome and L-dopachrome.

In some embodiments the melanin unit the melanin unit can comprise L-leucodopachrome and/or L-dopachrome.

In some embodiments the melanin unit can be of the structure:

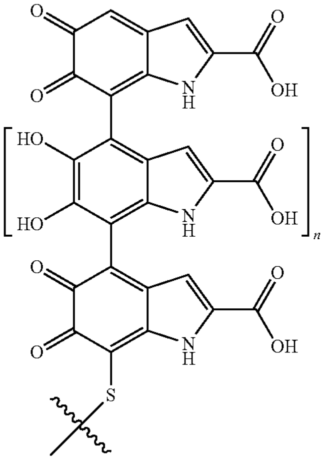

wherein n is an integer being at least 1 and wherein the S atom is the sulfur atom of a cysteine group of hydrolyzed keratin.

In some embodiments n can be between 1 and 100.

Alternatively, n may vary from 1 to a number of polymerized L-dope units, wherein the value is a function of oxidation and initial number of L-Dopa units. The actual number of melanin units may be determined by chemical and spectral analysis.

In numerous embodiments a KERMEL compound has a color and tone that is substantially similar to the color and tone of natural human skin or hair.

The term "substantially similar" implies a visual similarity of between the colors and tones skin and hair, and further, a quantified similarity as measured by RGB, CYMK or HEX coded color scale with the assistance of imaging technologies.

As has been exemplified in this application, in numerous embodiments a KERMEL compound has an orange-tan within the range of natural colors and tones of human skin or hair. And this range can be further expanded and modified by temperature conditions of the polymerization reaction at 40° C., 32° C. and 24° C. to produce distinct color groups.

In some embodiments a KERMEL compound can be modified to have a color and tone that is substantially similar to the color and tone of skin or hair of a given individual or a subject.

In some applications shown below the term "substantially similar" further implies a similarity of traits, such as moles, freckles, scars, pores and other minor skin imperfections, which can be captured and mapped by imaging technologies and accurately reproduced by a controlled application of high viscosity ink (HVKI) and KERMEL in the portable epidermis model (PEM).

In numerous embodiments a KERMEL compound or conjugate is provided in a form of a particulate matter or as a chromophoric particle.

In numerous embodiments the chromophore particle is a nanoparticle.

In numerous embodiments the nanoparticles can have a size in the range between about 50 nm to about 500 nm, and specifically in the range of about 50-500 nm, 100-450 nm, 150-400 nm and 200-350 nm, or in the range of about 50-100 nm, 100-200 nm, 200-300 nm, 300-400 nm and 400-500 nm.

In some embodiments the nanoparticles can have a size in the range between about 100 nm to 300 nm.

In some embodiments the nanoparticles can have a zeta potential of at least about −20 mV.

In some embodiments the nanoparticles can have a zeta potential of at least about −30 mV.

In some embodiments the nanoparticles can have a zeta potential of at least about −40 mV.

In some embodiments the nanoparticles can have a zeta potential in the range of at least about −20 mV to at least about 40 mV.

Thus, the invention can be further articulated in terms of a chromophore nanoparticle comprising or consisting of any one of the afore-mentioned KERMEL compounds.

The invention can be further articulated in terms of a composition of matter comprising or consisting of at least one KERMEL compound or conjugate as above.

In numerous embodiments the composition can further comprise at least one natural or synthetic pigment material.

In some embodiments the at least one natural or synthetic pigment material can be a melanin and a melanin derivative.

In some embodiments the melanin and the melanin derivative can be selected from eumelanin, pheomelanin, neuromelanin, allomelanin and pyomelaninis or a derivative of thereof, or any combination thereof.

One of the prospective applications of the present compositions is in cosmetics and specifically in cosmetic foundations and makeups or other beauty products comprising thereof.

Therefore, in numerous embodiments the cosmetic compositions of the invention can comprise additional pigments and coloring agents such as titanium dioxide (occasionally zinc oxide) combined with various combinations of black, umber or russet iron oxides to impart the desired color and tone.

Thus, the invention can be further articulated in terms of a pigment or coloring agent comprising or consisting of at least one KERMEL compound as above or the composition comprising thereof and optionally comprising one or more additional pigments or coloring agents that is used in cosmetics to impart a skin—or a hair-like color.

In some embodiments the pigment or the coloring agents of the invention can serve as tattoo inks for skin decoration.

In other words, the invention can also provide ink formulation, which can comprise a KERMEL compound or a pigment or a composition comprising thereof.

More broadly, the invention provides various types of color compositions, the unifying feature of which is the presence of one or more KERMEL compounds, and optionally other pigment compositions depending on the intended use.

In numerous embodiments the cosmetic compositions of the invention comprise a KERMEL compound, or the pigment or coloring agent of the invention, and water.

In numerous embodiments the water content of the compositions can be in the range between about 10% to about 90%, and specifically in the range of about 10%-90%, 20%-80%, 30%-70%, 40%-60%, or in the range of about 10%-20%, 20%-30%, 30%-40%, 40%-50%, 50%-60%, 60%-70%, 70%-80%, 70%-90%, or at least 10%, 20%, 30%, 40%, 50%, 60%, 70%, 80% and 90%.

In numerous embodiments the cosmetic compositions can comprise a KERMEL compound, or the pigment or coloring agent of the invention, and a cosmetically acceptable excipient.

In numerous embodiments the cosmetic compositions can further comprise at least one additional additive selected from UVA or UVB protecting agents, vitamins, nutrients, antioxidants, natural oils, topical debriding agents, skin cleansers, ointments, enzymes, excipients, emollients, humectants, preservatives, a free keratin, a free melanin or derivatives thereof.

In other words, one of the objectives of the invention is to provide compositions serving aesthetic and cosmetic purposes, using KERMEL compounds or pigments or coloring agents, or compositions comprising thereof.

In numerous embodiments the invention can provide cosmetic, skin care or skin beauty products comprising KERMEL compounds, pigments or compositions as above. The invention is compatible with water-based and oil-based products.

Therefore, in numerous embodiments the cosmetic products of the invention can be in the form of creams, emulsions, lotions, gels, make-ups, skin or hair coloring products and tattoo inks.

In some embodiments the cosmetic products of the invention can be personally customized to match the color and tone of a subject's skin or hair.

In other words, it is yet another objective of the invention to provide compositions for use in coloring or masking a region of a subject's skin or hair, the distinctive feature of which is that they comprise KERMEL compounds, pigments or compositions as above.

Still another objective of the invention is to provide compositions for use in coloring or masking a synthetic or a semi-synthetic skin in vivo or ex vivo that comprise KERMEL compounds, pigments or compositions as above.

This aspect can be further articulated in terms of use of KERMEL compounds in the manufacturing/preparation of a personally customized cosmetic product matching the color and tone of a subject's skin or hair.

And further, in terms of use of KERMEL compounds in a method of coloring or masking a skin region or a synthetic or a semi-synthetic skin in vivo or ex vivo.

It is another important objective of the invention to provide a method for producing pigment compositions. First and foremost, there is a process for making KERMEL, or a keratin-melanin conjugate of the invention, with an essential step of reacting an hydrolyzed keratin with a melanin precursor under oxidative conditions to allow formation of the keratin-melanin conjugate.

In some embodiments the process can comprise a step of hydrolyzing keratin.

In some embodiments the process can comprise reacting hydrolyzed keratin with a melanin precursor to bind said precursor to the keratin and thereby produce a melanin precursor-keratin compound.

In some embodiments the reacting occurs under oxidative conditions.

In some embodiments the melanin precursor can be L-tyrosine, L-DOPA or L-dopaquinone, or only L-DOPA.

In some embodiments the free SH groups are reacted to form the keratin-melanin conjugate as defined.

In some embodiments tyrosine groups are oxidized in the presence of an oxidizing agent such as tyrosinase.

In some embodiments the oxidized tyrosine reacts with cysteine and phenylalanine amino acids to form yellow and red pigments, respectively.

Thus, essentially in the process for forming a keratin-melanin conjugate of the invention, the conjugate can be provided in three different colors (or different pigments:

- black pigments by reacting SH groups in a hydrolyzed keratin with a L-Dopa,
- yellow pigments by reacting oxidized tyrosine groups in keratin with cysteines,
- red pigments by reacting oxidized tyrosine groups on keratin with phenylalanine.

In other words, in some embodiments the process can comprise oxidizing tyrosine groups present on the keratin backbone.

In some embodiments the oxidized tyrosine groups are reacted with amino acids.

In some embodiments the amino acids can be cysteine and phenylalanine.

In some embodiments the process is for forming a KEREMEL compound can comprise one or more steps of:

(1) reacting SH groups in a hydrolyzed keratin with a L-Dopa; and/or (2) reacting oxidized tyrosine groups in keratin with cysteines; and/or (3) reacting oxidized tyrosine groups in keratin with phenylalanine.

In some embodiments the colored compound can be a black pigment, a yellow pigment or a red pigment.

The invention further provides methods for producing pigment compositions, with an essential step of mixing precalculated amounts of at least two KERMEL compounds having different colors or tones to obtain intermediate or specifically desired colors. This process can be carefully calibrated and controlled by measuring the colors on one of the recognized color scales (RGB, CYMK or HEX coded or other).

In some embodiments the method can be used for producing a pigment composition that is substantially similar to the color and tone of a subject's skin or hair by mixing precalculated amounts of at least two KERMEL compounds having different colors or tones as measured using a recognized color scale.

In some embodiments the method can further comprise mixing at least one additional pigment material, a natural or a synthetic pigment material.

In some embodiments the entire process can take place in a reservoir. In other embodiments it can take place in a printing device.

It is yet another objective of the invention to provide a series of compositions and materials for medical and therapeutic uses.

In some embodiments KERMEL compounds and compositions can be used for preparing high viscosity keratin inks of the invention (HVKI).

In numerous embodiments HVKI comprise one or more KERMEL compounds as and compositions as above and optionally additional pigment materials.

In numerous embodiments HVKI further comprise water as a solvent or a diluent to obtain certain viscosity.

Inks for 3D printing generally have viscosities between 300 and 30,000 cPs.

Thus, in some embodiments HVKI can have a viscosity ranging from $10^3$ to $10^7$ cP, and specifically a viscosity in the range of about $10^3$-$10^7$, $10^3$-$10^6$, $10^3$-$10^5$, $10^3$-$10^4$, or a viscosity in the range of about $10^3$-$10^4$, $10^4$-$10^5$, $10^5$-$10^6$, $10^6$-$10^7$, or a viscosity of at least about $10^3$, $10^4$, $10^5$, $10^6$, $10^7$.

In embodiments HVKI can lower viscosities in the range of about 5 to 30 cP.

In some embodiments HVKI can further comprise at least one pigment material that is a natural or a synthetic pigment material.

In some embodiments KERMEL compounds and compositions can be used for preparing films of the invention, keratin-melanin films (KMFs).

In numerous embodiments KMF can comprise one or more KERMEL compounds or compositions or pigments and/or HVKI as above.

In numerous embodiments the films comprise HVKI, which with the aid of additive manufacturing technologies can provide more complex 3D structured products.

In some embodiments the films comprising the HVKI can further comprise a 3D structure that is substantially similar to the papillary dermo-epidermal junction structure of human skin.

In some embodiments the 3D structure can be present on one side of the film.

In other words, in some embodiments KERMEL compounds and compositions can be used for the manufacturing/preparation of epidermis-like skin structures closely mimicking the SC and RR layers of the human epidermis.

In numerous embodiments the epidermis-like skin structure can comprise one or more KERMEL compounds, compositions, pigments, HVKI inks and/or KMF films.

In some embodiments KERMEL compounds and compositions can be used for the manufacturing/preparation of a potable epidermal model of the invention (PEM), reproducing on one of its sides the 3D structure of the papillary dermo-epidermal junction (see below).

Thus, it is another objective to provide a potable epidermal model (PEM) comprising a two-sided stratum corneum (SC) like keratin-melanin layer with an upper face layer comprising a color, a tone and/or a trait that substantially similar to the color, tone and/or trait of a human skin or hair, and a lower face comprising a 3D structure that is substantially similar to the papillary dermo-epidermal junction structure of human skin.

In numerous embodiments PEM can comprise one or more KERMEL compounds, compositions, pigments, HVKI inks and/or KMF film of the invention.

In numerous embodiments PEM can comprise one or more KERMEL compounds.

In some embodiments PEM can have at least one color, tone and/or trait that is substantially similar to the color, tone and/or trait of a subject's skin or hair. The way to achieve similarities between color and tones of the skin and specific external skin traits have been previously discussed.

More broadly, one of the objectives of this invention has been to develop a skin mimicking system (or an artificial skin substitute or a "second skin") preserving the structure and functionality of the entire epidermis. The system essentially incorporates KERMEL compounds or compositions and/or PEM.

PEM is essentially a two-sided keratin-melanin SC-like layer that serves several functions: protecting against microorganisms, water loss, etc., controlling gas and water exchange, and is adapted to mimic the precise color and texture of individual skin traits. On its upper side, the keratin-melanin layer comprises skin tones and traits that originated from melanin, as in natural skin. On the lower side, it is composed of papillary dermo-epidermal junction structures serving as landing strip for fibroblast and keratinocytes and encouraging their reformation in a precise anatomical manner for proper growth and reconstitution of the human epidermis (RhE).

Thus, the skin mimicking system of the invention is essentially composed of or can comprise at least one of:

(1) a composition comprising or consisting of a compound comprising a keratin backbone bonded to a plurality of melanin units, each melanin unit having a structure derived from oxidation of L-Dopa onto a hydrolyzed cysteine moiety of the keratin backbone (KERMEL); and (2) a composite structure comprising a two-sided SC like keratin-melanin layer with an upper face layer comprising a color, a tone and/or a trait that substantially similar to the color, tone and/or trait of a human skin or hair, and a lower face comprising a 3D structure that is substantially similar to the papillary dermo-epidermal junction structure of human skin (potable epidermal model, PEM).

In some embodiments the lower face of PEM can serve as a substrate for migration, maintenance or proliferation of fibroblast and/or keratinocytes cell populations, thereby stimulating reformation and reconstitution of RhE.

In numerous embodiments the upper face of PEM comprises KERMEL.

In some embodiments KERMEL can further comprise at least one pigment material that is a natural or a synthetic pigment material.

In numerous embodiments the keratin backbone in KERMEL is constructed of modified hydrolyzed keratin covalently associated with a plurality of melanin units.

In some embodiments the keratin backbone comprises a plurality of sulfur groups, with a portion thereof being covalently associated with a plurality of melanin units.

In some embodiments the keratin backbone is a keratin-melanin conjugate derived from L-Dopa polymerization on a keratin backbone that comprises a plurality of melanin units covalently associated with a keratin molecule.

In some embodiments the melanin unit can comprise a melanin selected from at least one of eumelanin, pheomelanin, neuromelanin, allomelanin and pyomelaninis or a derivative thereof.

In some embodiments the melanin can be eumelanin or pheomelanin or a derivative or a combination thereof.

In some embodiments the melanin unit can comprise one or more repeating units selected from L-tyrosine, L-Dopa, L-dopaquinone, L-leucodopachrome and L-dopachrome.

In some embodiments the melanin unit can comprise L-leucodopachrome and/or L-dopachrome.

In some embodiments the melanin unit can have the structure:

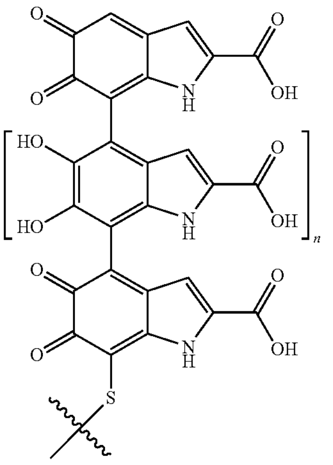

wherein n is an integer being at least 1 and wherein the S atom is the sulfur atom of a cysteine group of the hydrolyzed keratin.

In some embodiments n is between 1 and 100.

In some embodiments KERMEL can be provided in the form of a chromophore particle, and specifically nanoparticle, and more specifically a nanoparticle with a size in the range between about 50 nm to about 500 nm In other words, the system is a tunable system that can be adapted to the individual skin and hair tone, and further, has the potential to be incorporated into films, coatings, and printing for the pharma and cosmetic industries.

Thus, in some embodiments KERMEL can impart to the system at least one color, tone and/or trait that is substantially similar to the color, tone and/or trait of a subject's skin and hair.

More broadly, the system is a standalone structure predominantly composed of biomaterials naturally found in human skin. With the development of the high viscous keratin bio-ink and the assistance of additive manufacturing technologies, such as solvent casting, jet printing, screen printing, poly-jet and multi-jet printing, it enables to achieve epidermal-like 2D layout and 3D structure and thereby reconstitution of a structurally and functionally facsimile of human skin epidermis. It can be further adapted to match the exact texture, color and tone and the other characteristics of a subject's skin or hair.

In other words, the system of the invention is structurally adapted to function as an epidermal like structure or as a functional skin replacement or substitute, while reproducing individual outer skin characteristics. One of the important features of this system is in being configured for provide direct and unmediated contact with the surrounding living tissues. Due to its structural similarity to the skin epidermis, it can further serve as a substrate for growth, maintenance and proliferation of specific populations of cells, such as keratinocytes, lipid cells and stem cells, thus supporting additional important applications.

The system can be used for producing various types of skin replacement devices, such as skin grafts, implants and custom-made functional skin substitutes, and epidermis-like skin structures in general. The present application provides several examples of such applications.

In some embodiments the invention can provide skin grafts, implants or custom-made functional skin substitutes, or more generally epidermis-like skin structures, comprising the system as above.

In some embodiments the epidermis-like skin structures of the invention are bilateral.

In numerous embodiments they comprise on one of the sides a color, a tone and/or a trait that is substantially similar to the color, tone and/or trait of a subject's skin and hair.

In some embodiments they can comprise on the opposite side a 3D structure that is substantially similar to the papillary dermo-epidermal junction structures of human skin.

In some embodiments they can further comprise a plurality of cells, optionally fibroblast and/or keratinocytes.

In numerous embodiments the epidermis-like skin structures of the invention are made of or comprise HVKI inks and/or KMF film of the invention.

In other words, HVKI inks and the KMF film of the invention can serve the purpose or be used in methods of producing epidermis-like structures or artificial skin substitutes.

Essentially, a process of producing an epidermis-like skin structure uses HVKI that is applied on a back surface of a KMF film that comprises KERMEL on is top surface The application of HVKI involves generation of RR mimicking structures and can further involve incorporation of live cells. The production processes can be refined to include specific outward skin characteristics on the top KMF surface. (See also Nowogrodski et al. 2020. "Fabrication of second skin from keratin and melanin". Polymers 12:2568, herein incorporated in its entirety by reference).

Or in other words, the invention provides a process for forming an epidermis-like skin structure, which essentially involves applying a HVKI formulation on the back surface of a keratin-melanin film decorated or patterned on its front surface with an ink of a keratin-melanin conjugate, thus producing a bilayer epidermis-like skin structure.

In numerous embodiments the methods of making an artificial epidermis-like skin structure or a skin substitute comprise:

obtaining a KMF film of the invention, and applying onto one of its surfaces a HVKI of the invention.

In numerous embodiments HVKI can be applied onto the film by a deposition method selected from jet printing, screen printing or brushing.

In particle terms, it is another important objective of the invention to provide a series of artificial skin substitutes such as skin grafts or implants and custom-made functional skin substitutes.

In numerous embodiments such skin grafts, implants or custom-made functional skin substitutes can comprise KMF films of the invention.

In other embodiments they can comprise more complex epidermis-like structures of the invention, with KMF films and HVKI produced 3D structures.

In some embodiments the skin grafts, the implants or the custom-made functional skin substitutes can further comprise a plurality of cells, actives and/or enzymes.

In some embodiments the actives can be selected from antibiotics, antimycotic, antiviral, antiseptic, anti-inflammatory, immunomodulatory, analgesic agents, UVA or UVB protecting, vitamins, nutrients, antioxidants, natural oils, topical debriding agents, skin cleansers and ointments, dermal or epidermal cells, stem cells, excipients, emollients, humectants, preservatives.

In some embodiments the plurality of cells that are mesenchymal stem cells (MSC), optionally obtained from the subject that is supposed to receive the graft, the implant or the functional skin substitute.

In some embodiments the skin graft, the implant or the custom-made functional skin substitute can further comprise a chemotactic material inducing migration of MSC to the graft, the implant or the functional skin substitute.

The invention provides use of the system in the manufacturing/preparation of skin grafts, implants or custom-made functional skin substitutes.

Ultimately, the disclosed system, skin grafts, implants or skin substitutes can be implemented or used in methods of topical and intradermal drug delivery for replacing and/or treating damaged skin, wound healing and/or face or body re-shaping.

EXAMPLES

Any method and material similar or equivalent to those described herein can be used in the practice or testing of the present invention. Some embodiments of the invention will be now described by way of examples with reference to respective figures.

Example 1: KERMEL Synthesis

Figure 2:
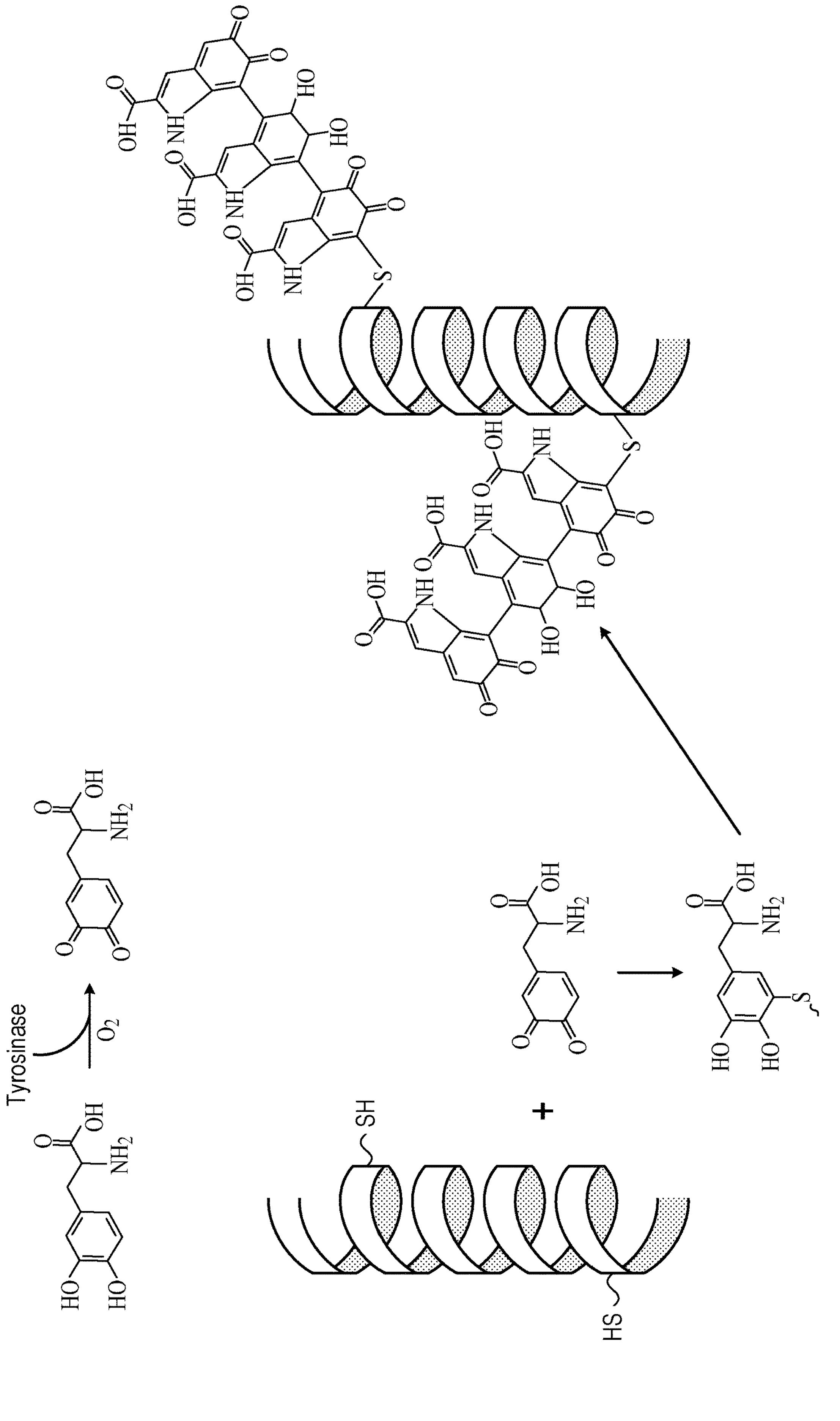
FIG. 2 illustrates the structure and the synthesis reaction of KERMEL from the hydrolyzed keratin and L-dopa building blocks.

A pre-set ready-to-use keratin/melanin color library was achieved using mixes of keratin/melanin chromophore nanoparticles (KERMEL) and synthetic eumelanin and pheomelanin. KERMEL is a novel molecule synthetized from L-dopa as the starting material of eumelanin and pheomelanin and hydrolyzed keratin, while preserving the hydrolyzed keratin properties with the two melanin color configurations. The color develops throughout the synthesis process and can be easily translated to a digitized color palette covering the entire range of the existing human skin colors and tones. Schematic illustrations of the KERMEL reaction and its potential applications in skin printing are provided in FIGS. 1 and 2.

Figure 3:
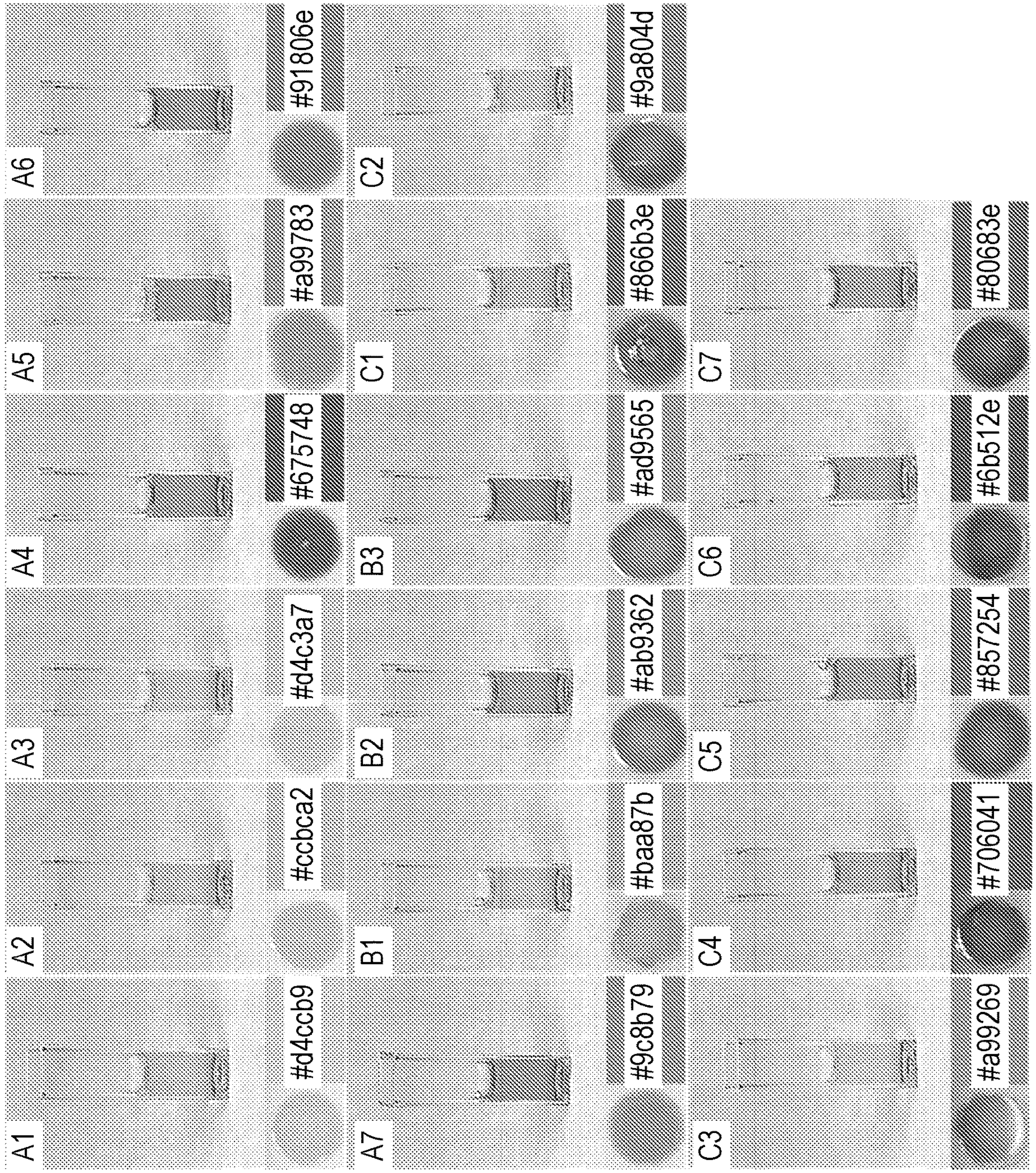
FIG. 3 illustrates further improvement of the KERMEL technology to extend the range of the obtained color tones. Figure shows 17 KERMEL solutions produced at 40° C. 32° C. and 24° C. (A, B and C groups), and their respective colors and tones on solid and extrapolated color palette of the calculated RGB to HEX color tones.
Figure 4A:
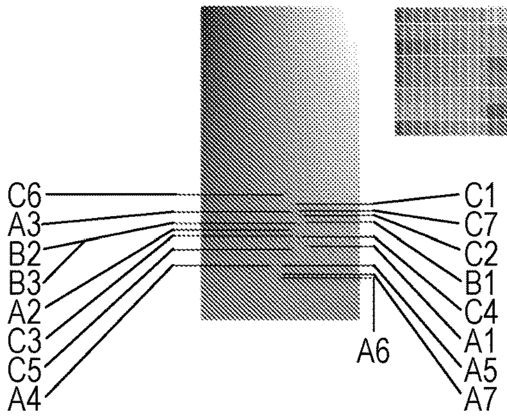
FIG. 4 illustrates the potential of the KERMEL technology to provide a full-range color palette. Figure shows (a) A to C colors groups positioned on the orange-tan color range of an RGB color palette; and (b) a calculated color palette of KERMEL mixes at eight points between two reactions.
Figure 4B:
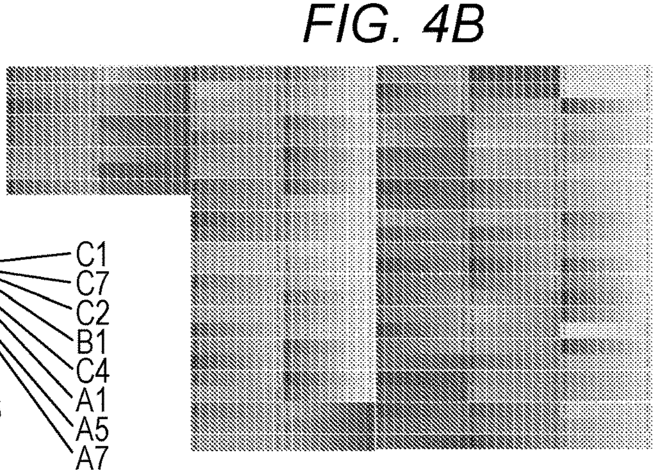
Figure 5A:
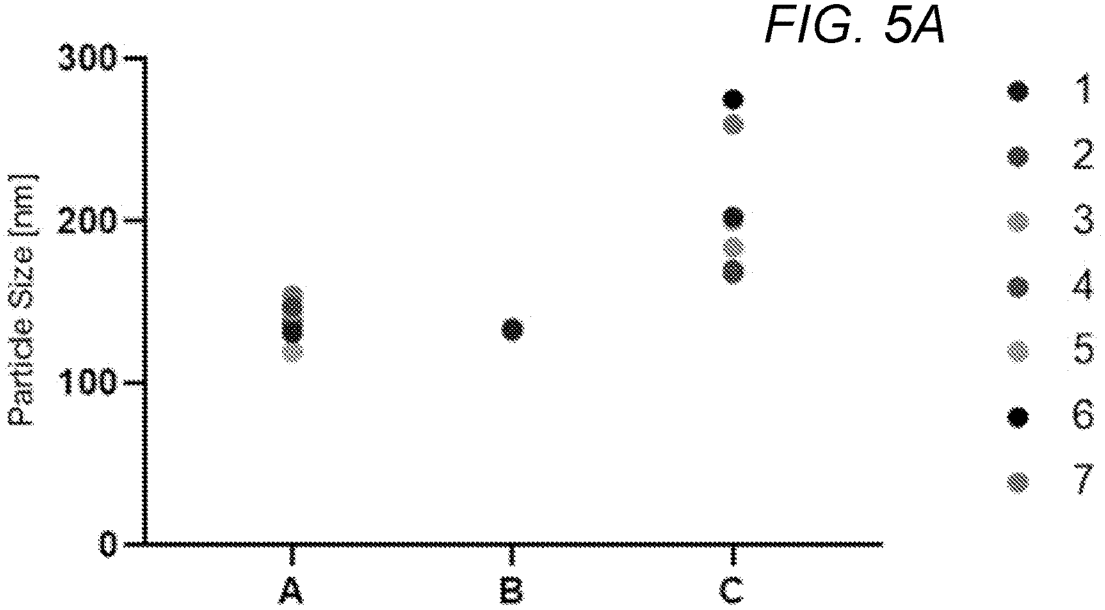
FIG. 5 illustrates one characteristic advantage of KERMEL which is high stability, as revealed by the measurements of particle size and zeta potential across the color groups A to C. Figure shows that the chromophore particles are (a) nanometric (around 100 to 300 nm) and (b) having a relatively low zeta potential (around-30 mV to −40 mV).
Figure 5B:
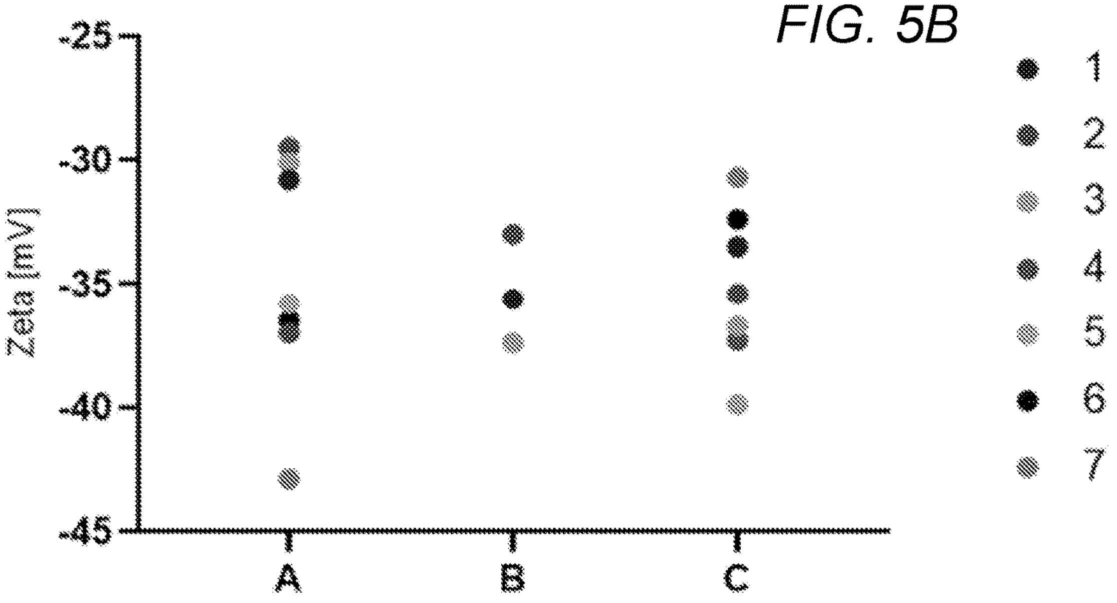

The reaction was performed using design of experiment (DOE) definitive screening design model to examine the effect of three parameters on color development: temperature, molar ratio of free sulfhydryl to L-Dopa and tyrosinase concentration. The experiment produced 17 color reactions divided into three color groups, A, B and C, as per 40° C., 32° C. and 24° C. reaction temperature conditions. FIG. 3 shows that all color groups fell within a range of orange-tan tones on the RGB and HEX color palettes. FIG. 4 further shows that a more complex and broad range of colors could be achieved by mixing calculated portions of A, B and C groups. The palette could be further expanded by calculated addition of synthetic pigments such as eumelanin and pheomelanin up to extent as to cover the entire range of the existing natural human skin colors and tones. FIG. 5 shows that KERMEL is made of chromophore particles characterized by a uniform nanometric size in the range of about 100 to 300 nm and a low zeta potential in the range of −30 mV to −40 mV, both suggesting durability and stability in water solutions.

Example 2: High Viscous Keratin Bio-Ink (HVKI

KERMEL can be useful per se for a variety of applications. It can further serve as basis for producing additional high-end products in the form of keratin/melanin films (KMFs) and high viscous keratin bio-ink (HVKI) for producing more complex skin mimicking structures with various degrees of sophistication.

An KMF essentially mimics the epidermal SC layer, and with the use of additive manufacturing technologies and HVKI can be further refined to form a composite mimicking the RR 3D structure to provide reconstruction of human epidermis (RhE).

Figure 6:
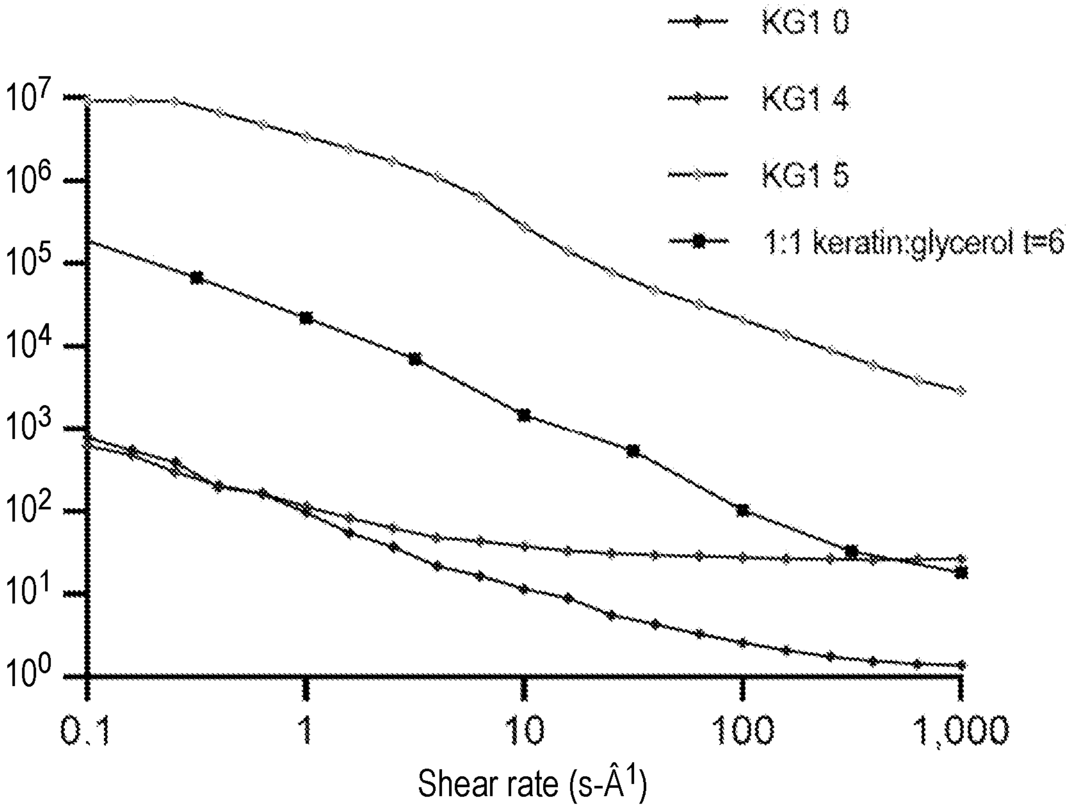
FIG. 6 another characteristic advantage of KERMEL which is viscosity evolution over time in the rotary evaporator. Figure shows viscosity analysis of high viscous keratin ink (HVKI), a secondary KERMEL product, with the time to achieve a paste-like material under evaporation rate 1.7 min/mL, temp. 40° C. and pressure 2 mbar standing on 6 min, 1:1 keratin:glycerol (■). Keratin concentration increased dramatically under increased water evaporation, and reached 20 to 30-fold increase with 90% water evaporated. Rheological behavior exhibited non-Newtonian shear thinning profiles with high zero shear viscosity.
Figure 7:
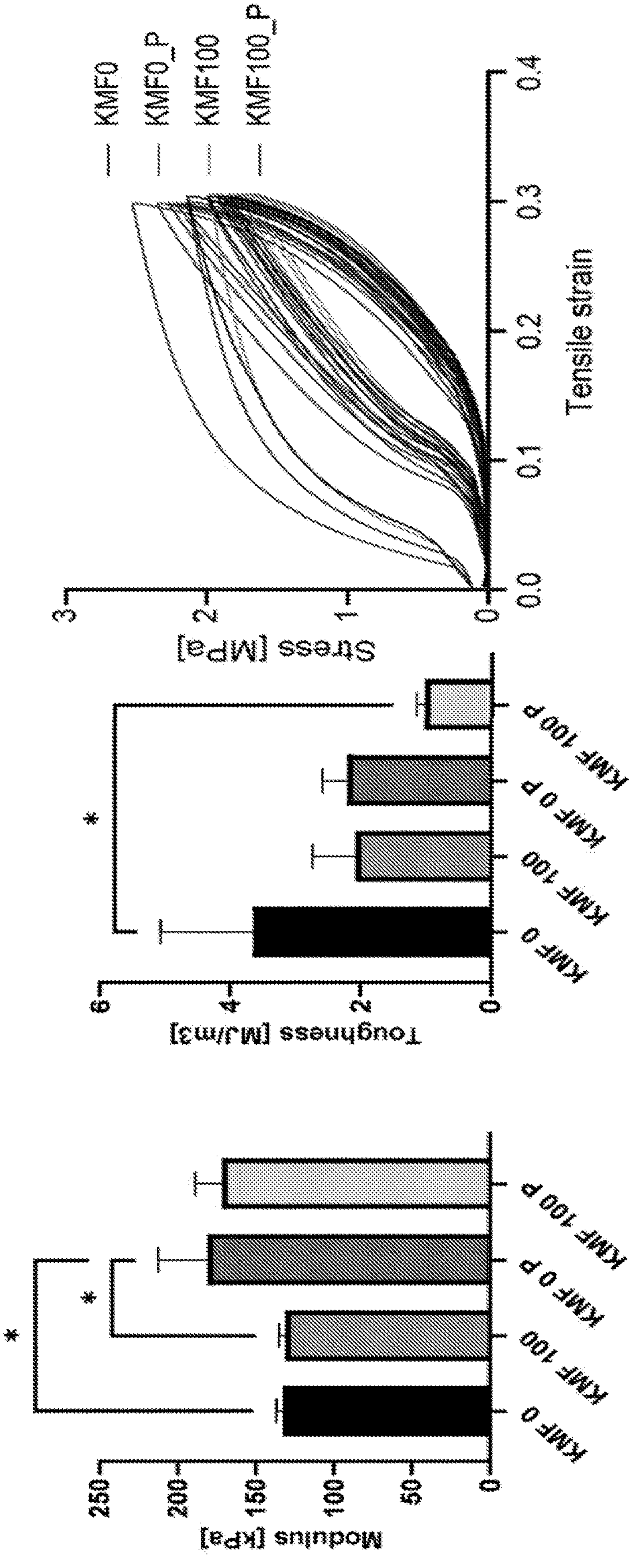
FIG. 7 illustrates mechanical properties of KERMEL films (KMFs) under cyclic tensions and forces mimicking the natural conditions of human skin. Figure shows KMFs cyclic tensile behavior with and without patterns at 50 mm/min, 30% strain, 5 rounds.
Figure 7:
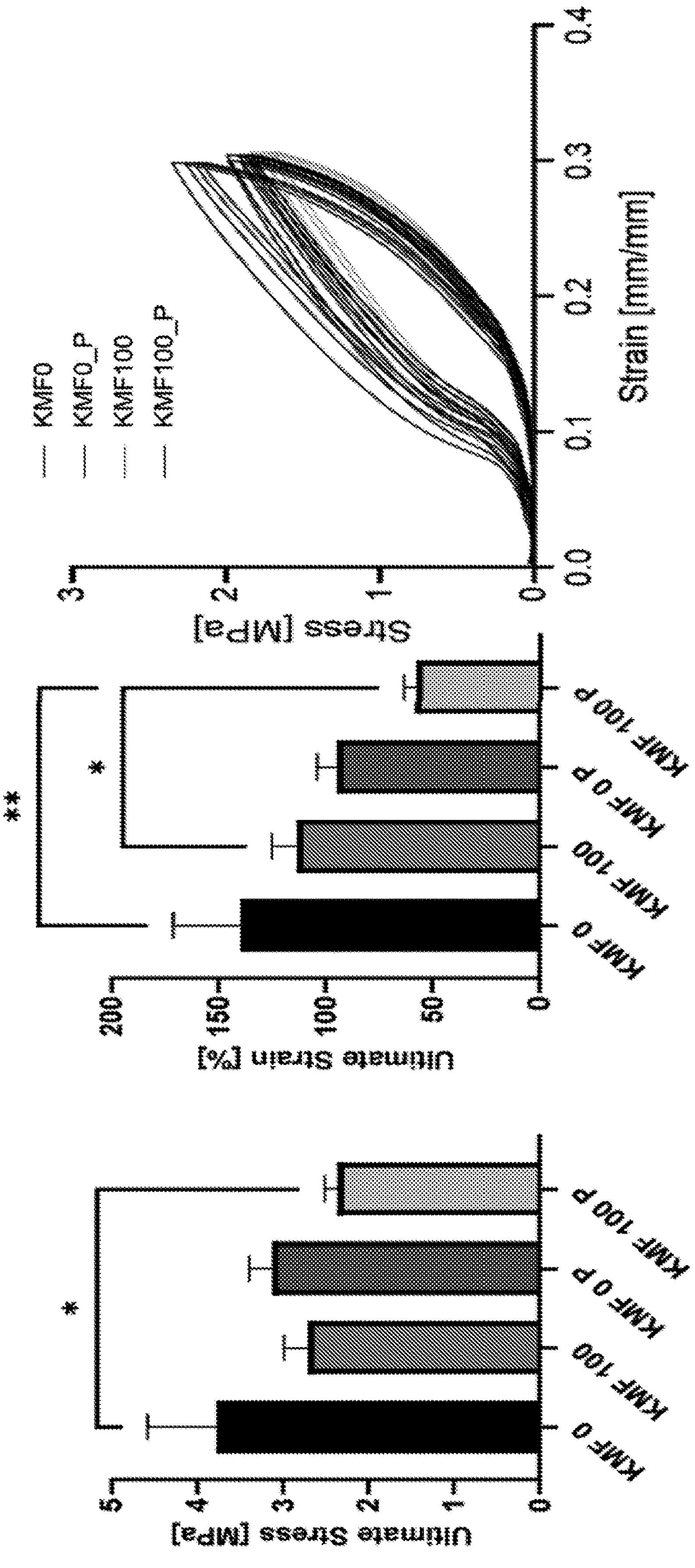
Figure 8:
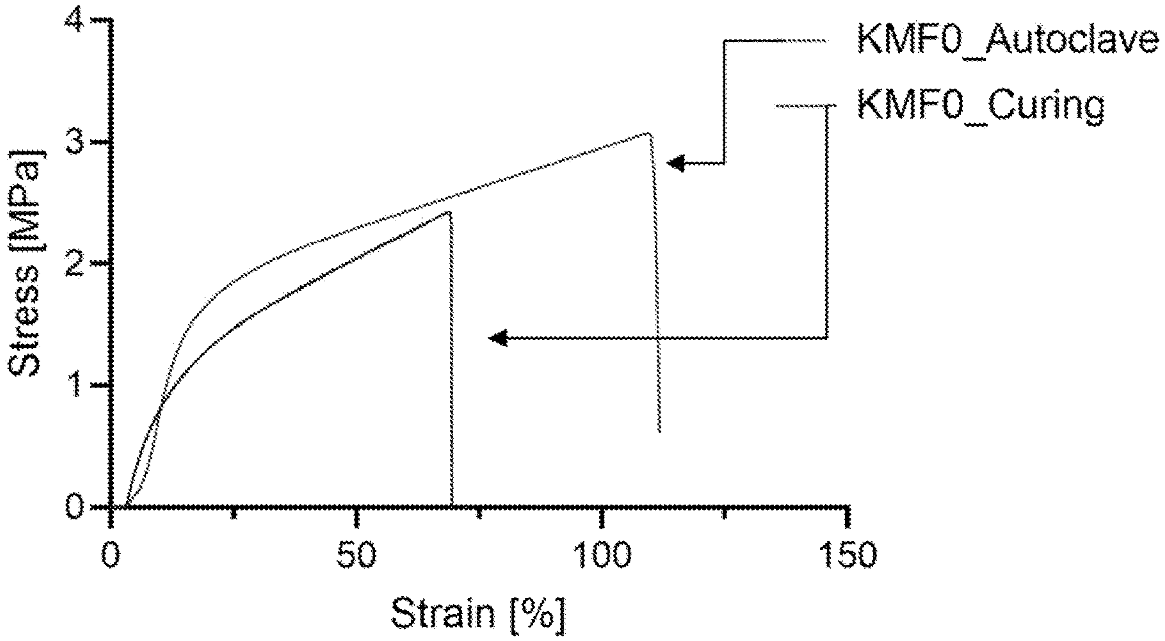
FIG. 8 illustrates further improvement of KMFs using an autoclave curing process. Figure shows a stress strain curve of KMF produced by the previous curing process and KMF produced in the wet autoclave.
Figure 9A:
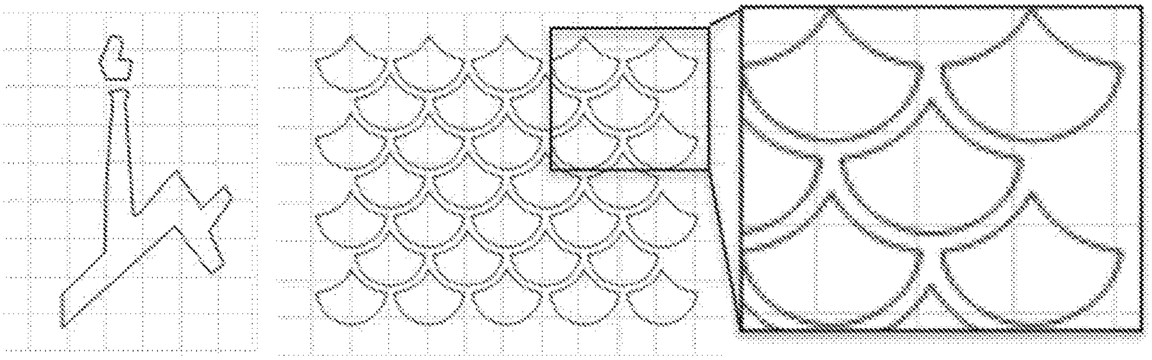
FIG. 9 illustrates a specific application of KERMEL using HVKI screen printing. Figure shows (a) the adopted patterns for screen printing, and (b) 2D resolution of the produced patterns.
Figure 9B:
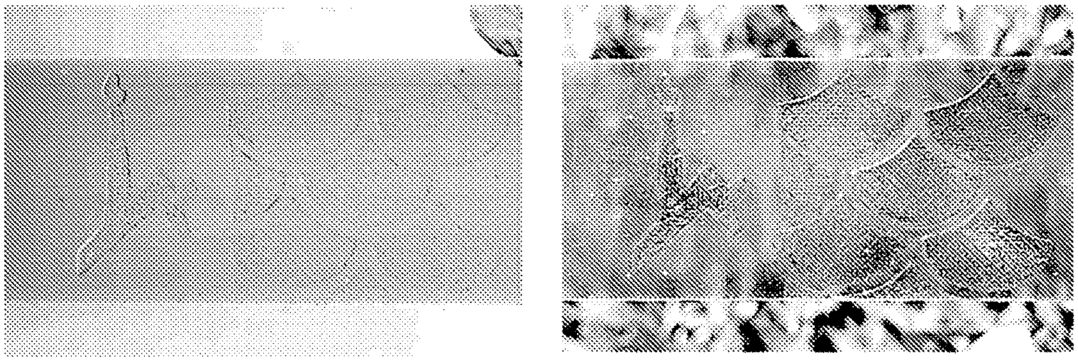

HVKI properties were evaluated in a series of experiments. FIG. 6 shows that the viscosity of HVKI can be controlled by careful monitoring of evaporation rate, temperature and pressure in the rotary evaporator. For example, a sufficiently viscous paste-like material (1:1 keratin:glycerol) can be achieved under certain conditions (evaporation rate 1.7 min/mL, temp. 40° C. and pressure 2 mbar) in the course of 6 min. Evaporation further had a significant effect on keratin concentrations, with 20 to 30-fold increase upon 90% water evaporated. Rheological behavior exhibited non-Newtonian shear thinning profiles with high zero shear viscosity. FIG. 7 shows some key properties of HVKI printed KMFs, suggesting that they can endure a range of cyclic tensions and stress forces mimicking the natural conditions of human skin. FIG. 8 shows that mechanical performance and other properties of KMFs can be further improved by specific curing processes, such as wet autoclaving for example. FIG. 9 exemplifies certain applications of KMFs and 3D HVKI printing to achieve refined composite structures.

Example 3: Viable Reconstructed Human Epidermis (RhE

Essentially, RhE reproduces the two main components of the human epidermis, with KMFs mimicking the SC layer and allowing color control and HVKI and screen printing mimicking the 3D structure of RR. The feasibility of making structurally and functionally competent RhE that would further allow perpetuation of natural skin processes was further evaluated.

FIG. 10 shows that HVKI is suitable for forming RR structures on glass, with viscosity highly impacting on the final 2D and 3D resolution and the compatibility of HVKI with screen printing methods. FIG. 11 shows the duration and proliferation of human epithelial keratinocytes (HEK) on KMFs. Cells were cultured on KMFs in the suitable medium with supplements and antibiotics in humidified environment at 37° C. and 5% $CO_2$. After reaching 70-80% confluency, cells were detached from the films by trypsin-EDTA and checked for preliminary cytocompatibility parameters of cellular proliferation and cytotoxicity by MTT assay relative to TCP control. The results have provided a proof-of-concept for a viable and competent RhE model produced by the presently developed methods and tools.

The invention claimed is:

1. A compound comprising a keratin backbone bonded to a plurality of melanin units, each melanin unit having a structure derived from oxidation of L-Dopa onto a hydrolyzed cysteine moiety of the keratin backbone (designated herein KERMEL).

2. The compound of claim 1, the keratin backbone is constructed of a modified hydrolyzed keratin that is covalently associated with a plurality of melanin units.

3. The compound of claim 1, wherein the keratin backbone is a keratin-melanin conjugate derived from L-Dopa polymerization on a keratin backbone that comprises a plurality of melanin units covalently associated with a keratin molecule.

4. The compound of claim 1, wherein the melanin unit is of the structure:

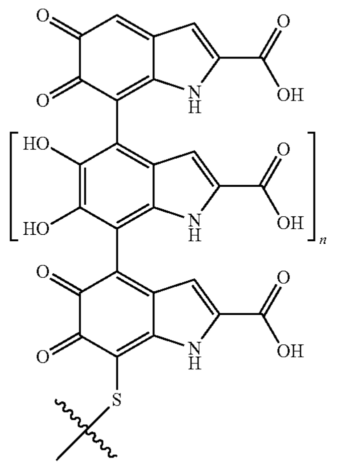

wherein n is an integer being at least 1 and wherein the S atom is the sulfur atom of a cysteine group of the hydrolyzed keratin.

5. A chromophore nanoparticle comprising or consisting of the compound of claim 1.

6. A composition of matter comprising or consisting of at least one compound claim 1, the composition being optionally a cosmetic, a skin care or a skin beauty product, or a composition for use in coloring or masking a region of a subject's skin or hair.

7. A skin pigment or coloring agent comprising or consisting of at least one compound of claim 1.

8. A method for producing a pigment composition that is substantially similar to the color and tone of a subject's skin or hair, the method comprises mixing precalculated amounts of at least two compounds of claim 1 having different colors or tones as measured using a recognized color scale, and optionally further mixing a pigment material that is a natural or a synthetic pigment material.

9. A high viscosity keratin ink (HVKI) comprising at least one compound of claim 1 and water.

10. A film comprising at least one compound of claim 1.

11. An epidermis-like skin structure comprising the HVKI of claim 9 and a film.

12. The epidermis-like skin structure of claim 11, the film comprising at least one compound comprising a keratin backbone bonded to a plurality of melanin units, each melanin unit having a structure derived from oxidation of L-Dopa onto a hydrolyzed cysteine moiety of the keratin backbone (designated herein KERMEL).

13. A portable epidermal model (PEM) comprising a two-sided stratum corneum (SC) like keratin-melanin layer with an upper face layer comprising a color, a tone and/or a trait that substantially similar to the color, tone and/or trait of a human skin or hair, and a lower face comprising a 3D structure that is substantially similar to the papillary dermo-epidermal junction structure of human skin, the PEM comprises at least one of at least one compound of claim 1.

14. A skin mimicking system comprising at least one of:

(1) a composition comprising or consisting of a compound comprising a keratin backbone bonded to a plurality of melanin units, each melanin unit having a structure derived from oxidation of L-Dopa onto a hydrolyzed cysteine moiety of the keratin backbone (KERMEL); and (2) a composite structure comprising a two-sided SC like keratin-melanin layer with an upper face layer comprising a color, a tone and/or a trait that substantially similar to the color, tone and/or trait of a human skin or hair, and a lower face comprising a 3D structure that is substantially similar to the papillary dermo-epidermal junction structure of human skin (potable epidermal model, PEM).

15. A method of making an artificial epidermis-like skin structure or a skin substitute, the method comprising:

applying the HVKI of claim 9 onto one of the surfaces of a film.

16. The method of claim 15, the film comprising at least one compound comprising a keratin backbone bonded to a plurality of melanin units, each melanin unit having a structure derived from oxidation of L-Dopa onto a hydrolyzed cysteine moiety of the keratin backbone (designated herein KERMEL).

17. An epidermis-like skin structure prepared by the method of claim 15.

18. A skin graft or an implant or a custom-made functional skin substitute comprising the epidermis-like structure of claim 11.

19. The skin graft, the implant or the custom-made functional skin substitute of claim 18, further comprising a plurality of cells and/or at least one active or enzyme.

20. The skin graft, the implant or the custom-made functional skin substitute of claim 19, with the at least one active being is selected from antibiotics, antimycotic, antiviral, antiseptic, anti-inflammatory, immunomodulatory, analgesic agents, UVA or UVB protecting, vitamins, nutrients, antioxidants, natural oils, topical debriding agents, skin cleansers and ointments, dermal or epidermal cells, stem cells, excipients, emollients, humectants, preservatives.

* * * * *